United States Patent
Burke et al.

(10) Patent No.: US 7,261,880 B2
(45) Date of Patent: Aug. 28, 2007

(54) METHODS OF TREATING SYNDROME X WITH ALIPHATIC POLYAMINES

(75) Inventors: Steven K. Burke, Sudbury, MA (US); Joanne M. Donovan, Needham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/125,701

(22) Filed: Apr. 17, 2002

(65) Prior Publication Data

US 2003/0049226 A1  Mar. 13, 2003

Related U.S. Application Data

(60) Provisional application No. 60/355,917, filed on Feb. 11, 2002, provisional application No. 60/284,445, filed on Apr. 18, 2001.

(51) Int. Cl.
*A61K 31/74* (2006.01)
*A61K 31/785* (2006.01)

(52) U.S. Cl. .................. 424/78.31; 424/78.35

(58) Field of Classification Search ............ 424/78.31, 424/78.35, 78.3
See application file for complete search history.

(56) References Cited

U.S. PATENT DOCUMENTS 4,231,938 A  11/1980  Monaghan et al. ...... 260/343.5

(Continued)

FOREIGN PATENT DOCUMENTS

EP  1 092 711  * 4/2001

(Continued)

OTHER PUBLICATIONS

Press Release—Pharmaceutical Industry, GelTex Pharmaceuticals, Inc., May 31, 2000 "FDA Approves Welchol (Colesevelam) Lipid-Lowering Agent.".*

(Continued)

*Primary Examiner*—Michael G. Hartley
*Assistant Examiner*—Blessing Fubara
(74) *Attorney, Agent, or Firm*—Hamilton, Brook, Smith & Reynolds, P.C.

(57) ABSTRACT

The invention relates to a method for treating Syndrome X, or inhibiting the onset of symptoms of Syndrome X in a patient, and includes administering a therapeutically effective amount of a salt of at least one alkylated and cross-linked polymer, or a copolymer thereof, the polymer salt formed as a product of the reaction of one or more polymers, or salts and copolymers thereof, having a repeat unit that is essentially:

$$-(CH_2-CH)_n- \quad (1)$$
$$\phantom{-(CH_2-CH)_n-}|$$
$$\phantom{-(CH_2-CH)_n-}CH_2$$
$$\phantom{-(CH_2-CH)_n-}|$$
$$\phantom{-(CH_2-CH)_n-}NR_2 \quad \text{or}$$

$$-(CH_2-CH)_n- \quad (2)$$
$$\phantom{-(CH_2-CH)_n-}|$$
$$\phantom{-(CH_2-CH)_n-}NR_2$$

where n is a positive integer and each R, independently, is H or a $C_1$–$C_8$ alkyl group; at least one aliphatic alkylating agent; and a cross-linking agent. Long term administration of the cross-linked polyamine salts of the invention increases HDL levels and decreases LDL levels in patients. The invention also provides for administration of the polymer salt colesevelam, in combination with an HMG-CoA reductase inhibitor; the combined administration is effective in further lowering serum total-cholesterol and LDL-cholesterol levels beyond that achieved by either agent alone.

2 Claims, 2 Drawing Sheets

U.S. PATENT DOCUMENTS

| | | | |
|---|---|---|---|
| 4,346,227 A | 8/1982 | Terahara et al. | 560/119 |
| 4,444,784 A | 4/1984 | Hoffman et al. | 424/279 |
| 5,177,080 A | 1/1993 | Angerbauer et al. | 514/277 |
| 5,273,995 A | 12/1993 | Roth | 514/422 |
| 5,354,772 A | 10/1994 | Kathawala | 514/414 |
| 5,468,727 A | 11/1995 | Phillips et al. | |
| 5,487,888 A | 1/1996 | Mandeville, III et al. | 424/78.1 |
| 5,496,545 A | 3/1996 | Holmes-Farley et al. | 424/78.11 |
| 5,607,669 A | 3/1997 | Mandeville, III et al. | 424/78.12 |
| 5,618,530 A | 4/1997 | Mandeville, III et al. | 424/78.12 |
| 5,624,963 A | 4/1997 | Mandeville, III et al. | 514/789 |
| 5,667,775 A | 9/1997 | Holmes-Farley et al. | 424/78.11 |
| 5,679,717 A | 10/1997 | Mandeville, III et al. | 514/742 |
| 5,693,675 A * | 12/1997 | Mandeville, III et al. | 514/742 |
| 5,702,696 A | 12/1997 | Mandeville, III et al. | 424/78.12 |
| 5,703,188 A | 12/1997 | Mandeville, III et al. | 526/290 |
| 5,840,766 A | 11/1998 | Mandeville, III et al. | 514/742 |
| 5,900,475 A | 5/1999 | Mandeville, III et al. | 528/392 |
| 5,917,007 A | 6/1999 | Mandeville, III et al. | 528/421 |
| 5,919,832 A | 7/1999 | Mandeville, III et al. | 521/36 |
| 5,925,379 A | 7/1999 | Mandeville, III et al. | 424/484 |
| 5,929,184 A | 7/1999 | Holmes-Farley et al. | 526/290 |
| 5,969,090 A | 10/1999 | Mandeville, III et al. | 528/392 |
| 5,981,693 A | 11/1999 | Mandeville, III et al. | 528/339.3 |
| 5,985,935 A | 11/1999 | Kharazmi et al. | |
| 6,007,803 A | 12/1999 | Mandeville, III et al. | |
| 6,034,129 A | 3/2000 | Mandeville, III et al. | 514/549 |
| 6,060,517 A | 5/2000 | Mandeville, III et al. | 514/742 |
| 6,066,678 A | 5/2000 | Mandeville, III et al. | 514/742 |
| 6,083,495 A | 7/2000 | Holmes-Farley et al. | 424/78.1 |
| 6,083,497 A | 7/2000 | Huval et al. | 424/78.35 |
| 6,129,910 A | 10/2000 | Holmes-Farley et al. | 424/78.12 |
| 6,177,478 B1 | 1/2001 | Holmes-Farley et al. | 514/789 |
| 6,190,649 B1 | 2/2001 | Holmes-Farley et al. | 424/78.08 |
| 6,203,785 B1 | 3/2001 | Holmes-Farley et al. | 424/78.18 |
| 6,225,355 B1 | 5/2001 | Mandeville, III et al. | 514/742 |
| 6,248,318 B1 | 6/2001 | Huval et al. | 424/78.35 |
| 6,264,937 B1 | 7/2001 | Mandeville, III et al. | |
| 6,271,264 B1 | 8/2001 | Dhal et al. | 514/642 |
| 6,281,252 B1 | 8/2001 | Holmes-Farley et al. | |
| 6,290,947 B1 | 9/2001 | Fitzpatrick et al. | |
| 6,294,163 B1 | 9/2001 | Dhal et al. | 424/78.01 |
| 6,423,754 B1 | 7/2002 | Holmes-Farley et al. | |
| 6,627,636 B2 * | 9/2003 | Robl | 514/291 |
| 2001/0044519 A1 | 11/2001 | Mandeville, III et al. | |
| 2001/0051660 A1 | 12/2001 | Holmes-Farley et al. | |
| 2002/0095002 A1 | 7/2002 | Mandeville, III et al. | |
| 2002/0198202 A1 | 12/2002 | Gwynne et al. | |

FOREIGN PATENT DOCUMENTS

| | | |
|---|---|---|
| WO | WO84/02131 | 6/1984 |
| WO | WO92/10522 | 6/1992 |
| WO | WO94/27621 | 12/1994 |
| WO | WO95/34585 | 12/1995 |
| WO | WO95/34588 | 12/1995 |
| WO | WO96/21454 | 7/1996 |
| WO | WO96/39449 | 12/1996 |
| WO | WO 98/57652 | 12/1998 |
| WO | WO98/57652 * | 12/1998 |
| WO | WO99/15186 | 4/1999 |
| WO | WO99/22744 | 5/1999 |
| WO | WO99/34787 | 7/1999 |
| WO | WO 00/38723 | 7/2000 |
| WO | WO 00/38728 | 7/2000 |
| WO | WO 00/64920 | 11/2000 |
| WO | WO 01/03705 | 1/2001 |
| WO | WO 01/25291 A1 | 4/2001 |

OTHER PUBLICATIONS

Chertow, G.M. et al. "Long-term effects of sevelamer hydrochloride on the calcium X phosphate product and lipid profile of haemodialysis patients," *Nephrol. Dial. Transplant.* 14:2907-2914 (1999).

Chertow, G.M. et al., "A randomized trial of sevelamer hydrochloride (RenaGel) with and without supplemental calcium: Strategies for the control of hyperphosphatemia in hemodialysis patients," *Clin. Nephrol.* 51(1):18-26 (1999).

Bleyer, A.J. et al., "A Comparison of the Calcium-Free Phosphate Binder Sevelamer Hydrochloride With Calcium Acetate in the Treatment of Hyperphosphatemia in Hemodialysis Patients," *Am. J. Kid. Dis.* 33(4):694-701 (1999).

Collins, A.J. et al. "Hospitalization risks between Renagel phosphate binder treated and non-Renagel treated patients," *Clin. Nephrol.* 54(4):334-341 (2000).

Burke, S.K., "Renagel®: reducing serum phosphorus in haemodialysis patients," *Hospital Medicine* 61(9):1-6 (Sep. 2000).

Goldberg, D.I., et al. "Effect of RenaGel®, a non-absorbed, calcium- and aluminium-free phosphate binder, on serum phosphorous, calcium, and intact parathyroid hormone in end-stage renal disease patients," *Nephrol. Dial. Transplant.* 13:2303-2310 (1998).

Burke, S.K. et al., "Renagel®, A Calcium and Aluminum Free Phosphate Binder Inhibits Phosphate Absorption in Normal Volunteers," Abstract, *Bone and Mineral Metabolism*, A40, *Nephrol. Dial. Transplant.* 11(6) (1996).

Burke, S.K. et al., "Renagel®, A Calcium and Aluminum Free Phosphate Binder Lowers Serum Phosphorous in Hemodialysis Patients," Abstract, *Bone and Mineral Metabolism*, A41, *Nephrol. Dial. Transplantat.* 11(6) (1996).

Slatopolsky, E. et al., "Effect of Renagel™, A Novel Phosphate Binder, on Serum Phosphorous and Parathyroid Hormone Levels in End Stage Renal Disease (ESRD) Patients," Abstract A2859, *Mineral Metabolism: Mineral-Related Hormones/Factors, J. Am. Soc. Nephrol.*, 7:1818 (1996).

Chertow, G.M. et al., "Poly [allylamine] hydrochloride (renagel®) [RG] with and without supplemental calcium [C] for hyperphosphatemia [HP] in ESRD," Abstract A2559, *Mineral Metabolism: Bone Disease, J. Am. Soc. Nephrol.*, 8:549A (1996).

Burke, S.K. et al., "RenaGel®, a novel calcium- and aluminum-free phosphate binder, inhibits phosphate absorption in normal volunteers," *Nephrol. Dial. Transplant.* 12:1640-1644 (1997).

Burke, S.K. et al., "RenaGel® Lowers Serum Phosphorous and Intact Parathyroid Hormone in Hemodialysis Patients," Abstract. Paper presented at the meeting of the *National Kidney Foundation*, San Antonio, TX (Apr. 1997).

Reiner, D. et al., "Efficacy of a nonabsorbable phosphate binder for the treatment of hyperphosphatemia in chronic hemodialysis patients," Abstract A2636, *Mineral Metabolism: Calcium/ Magnesium/Phosphorous, J. Am. Soc. Nephrol.* 8:566A (1997).

Chertow, G.M. et al., "A Randomized Trial of Sevelamer Hydrochloride (RenaGel) with and without Supplemental Calcium: Strategies for the Control of Hyperphosphatemia and Hyperparathyroidism in Hemodialysis Patients." Presented at the *American Society of Nephrology*, 30th Annual Meeting, Nov. 2-5, 1997.

Chertow, G.M. et al., "A Long-term Study of the Effectiveness of Sevelamer Hydrochloride (RenaGel) in Hemodialysis Patients," Abstract A2820, *Mineral Metabolism: Calcium/Magnesium/Phosphorous, J. Am. Soc. Nephrol.* 9:552A (Sep. 1998) Program and Abstracts Issue.

Wilkes, B.M. et al., "Simultaneous lowering of serum phosphate and LDL-cholesterol by sevelamer hydrochloride (RenaGel) in dialysis patients," *Clini. Nephrol.* 50(6):381-386 (1998).

Chertow, G.M. et al., "Poly[allylamine Hydrochloride] (RenaGel): A Noncalcemic Phosphate Binder for the Treatment of Hyperphosphatemia in Chronic Renal Failure," *Am. J. Kid. Dis.*, 29(1):66-71 (1997).

Slatopolsky, E.A., et al., "RenaGel™, a nonabsorbed calcium- and aluminum-free phosphate binder, lowers serum phosphorus and parathyroid hormone," *Kid. Internat.*, 55:299-307 (1999).

Burke, S.K. et al., "Control of Pi with RenaGel™, a Calcium and Aluminum Free Phosphate Binder, Combined with Vitamin D Stabilizes ipth in Esrd Independent of CA," 14TH International Congress of Nephrology, Abstract P435, *Nephrology* 3:5183 (1997).

Bleyer, A.J. et al. "An open label, cross-over study of the new phosphate binder RenaGel™ in the management of hyperphosphatemia in ESRD patients," Abstract A2554, *Mineral Metabolism: Bone Disease, J. Am. Soc. Nephrol.* 8:548A (1997).

Davidson, M. et al., "Colesevelam Hcl (Welchol™), a new, potent, well tolerated non systemic, lipid lowering agent." Abstract TuP2:W16 Poster Abstracts: New Abstracts of Pharnacological Treatment, *XIIth International Symposium on Atherosclerosis*, Stockholm, Sweden, (Jun. 25-29, 2000).

Mesner, C.H. et al., "Cholestagel for the Treatment of Hypercholesterolemia," Abstract. Presented at XIII International Symposium on Drug Altering Lipid Metabolism, Florence, Italy, May 30-Jun. 3, 1998. Page 59 of abstract book.

Wilson, T.A. et al., "Studies of cholesterol and bile acid metabolism, and early atherogenesis in hamsters fed GT16-239, a novel bile acid sequestrant (BAS)," *Atherosclerosis* 140:315-324 (1998).

Shepherd et al., "Cholestyramine Promotes Receptor-Mediated Low-Density-Lipoprotein Catabolism," *New Engl. J. Med.* 302(22):1219-1222 (1980).

Davidson, M.H. et al., "Low-Dose Combination Therapy with Colesevelam Hydrochloride and Lovastatin Effectively Decreases Low-Density Lipoprotein Cholesterol in Patients with Primary Hypercholesterolemia," *Clin. Cardiol.* 24:467-474 (2001).

Hunninghake, D. et al., "Coadministration of colesevelam hydrochloride with atorvastatin lowers LDL cholesterol additively," *Atherosclerosis* 158:407-416 (2001).

Insull, W., Jr. et al., "Effectiveness of Colesevelam Hydrochloride in Decreasing LDL Cholesterol in Patients With Primary Hypercholesterolemia: A 24-Week Randomized Controlled Trial," *Mayo Clin. Proc.* 76:971-982 (2001).

Davidson, M.H. et al., "Colesevelam Hydrochloride: (Cholestagel) A New, Potent Bile Acid Sequestrant Associated With a Low Incidence of Gastrointestinal Side Effects," *Arch. Intern. Med.* 159:1893-1900 (Sep. 1999).

Ose, L. et al., "Once Per Day and Split Dosing of Colesevelam in Patients with Type IIa Hypercholesterolemia," Abstract. Presented at the 5th International Symposium on Multiple Risk Factors in Cardiovascular Disease: Global Assessment and Intervention, Venice, Italy, Oct. 28-31, 1999. Page 120 of abstract book.

Mesner, C.H. et al., "Effect of Cholestagel® and Lovastatin Alone and in Combination for the Treatment of Hypercholesterolemia," Abstract. Presented at XIII International Symposium on Drug Altering Lipid Metabolism, Florence, Italy, May 30-Jun. 3, 1998. Page 60 of abstract book.

Stampfer et al.,"A Prospective Study of Cholesterol, Apolipoproteins, and the Risk of Myocardial Infarction," *New England J. Med.* 325:373-381 (1991).

Kannel et al. "Cholesterol in the Prediction of Atherosclerotic Disease," *Ann. Internal Med.* 90:85-91 (1979).

Gordon et al., "High Density Lipoprotein As a Protective Factor Against Coronary Heart Disease," The Framingham Study, *Am. J. Med.* 62:707-714 (1977).

Yalpani, M., "Cholesterol Lowering Drugs," *Chemistry and Industry* pp. 85-89 (Feb. 5, 1996).

"Hypolipidemics," *Physicians' Desk Reference 50th ed.*, Medical Economics co.:216 (1996).

Grundy, et al., "Interruption of the enterohepatic circulation of bile acids in man: Comparative effects of cholestyramine and ileal exclusion on cholesterol metabolism," *J. Lab. Clin. Med.* 78:94-121 (1971).

Wizeman, W.J., and Kofinas, P., "Molecularly Imprinted Polymer Hydrogels Displaying Isomerically Resolved Glucose Binding," *Biomaterials*, 22: 1485-1491 (2001).

Garg, A., and Grundy, S.M., "Cholestyramine Therapy for Dyslipidemia in Non-Insulin Diabetes Mellitus: A Short-Term, Double-Blind, Crossover Trial," *Annals of Internal Medicine*, 121(6): 416-422 (1994).

"Dietary Guidelines for Americans," *Home and Garden Bulletin No. 232* (Fifth Edition), (2000).

Clinical Study Report generated by "The SAS System," (Mar. 23, 2000).

* cited by examiner

METHODS OF TREATING SYNDROME X WITH ALIPHATIC POLYAMINES

RELATED APPLICATION(S)

This application claims the benefit of U.S. Provisional Application No. 60/284,445, filed on Apr. 18, 2001 and U.S. Provisional Application No. 60/355,917, filed Feb. 11, 2002. The entire teachings of the above application(s) are incorporated herein by reference.

BACKGROUND OF THE INVENTION

Syndrome X is a combination of metabolic disorders that typically include elevated triglycerides (TG), elevated glycemia, decreased high density lipoprotein cholesterol (HDL), insulin resistance, hyperinsulinemia, high blood pressure, increased plasma uric acid levels, and central body obesity. Individuals with Syndrome X have an increased risk of peripheral vascular and coronary artery disease. Research has shown that individuals who are insulin resistant and hyperinsulinemic are more likely to develop glucose intolerance, hypertension, and hyperlipidemia, characterized by high plasma TG and low HDL levels. Low HDL levels, insulin resistance, and hypertension are significant risk factors for the development of heart disease. In contrast, increased levels of HDL are associated with lower risks of coronary heart disease (Stampfer, et al., *New England J. Med.* 325:373–381(1991); Kannel, et al., *Ann. Internal Med.* 90:85–91 (1979); and Gordon, et al., *Am. I. Med.* 62:707–714 (1977)). Thus, a need exists for new methods for treating Syndrome X and for inhibiting the onset of symptoms of Syndrome X in humans and other animals.

SUMMARY OF THE INVENTION

The present invention relates to the discovery that the long term administration of certain aliphatic polyamine polymers, such as colesevelam, increases HDL and decreases LDL levels in individuals. As such, one embodiment of the invention provides a method for treating Syndrome X by administering the aliphatic polyamine resins to the gastrointestinal tract of the patient.

One embodiment of the invention includes a treatment for Syndrome X in a human or nonhuman patient that exhibits one or more of the symptoms of Syndrome X, or that exhibits one or more of the symptoms of the metabolic disorders that characterize Syndrome X, by administering at least one polymer salt of the invention to the gastrointestinal tract. Another embodiment includes a prophylaxis or method of inhibiting the onset of the symptoms of Syndrome X, or method of inhibiting the onset of one or more of the symptoms of the metabolic disorders that characterize Syndrome X, by administering at least one polymer salt of the invention to the gastrointestinal tract.

According to an embodiment, a method for treating Syndrome X or inhibiting the onset of symptoms of Syndrome X in a patient includes administering to the gastrointestinal tract a therapeutically effective amount of the salt of at least one aliphatic amine polymer, such as an alkylated and/or cross-linked polymer, or a copolymer thereof, the polymer salt formed as a reaction product of the reaction of one or more polymers, or salts and copolymers thereof, having a repeat unit that is essentially:

where n is a positive integer and each R, independently, is H or a $C_1$–$C_8$ alkyl group; at least one aliphatic alkylating agent; and a cross-linking agent. According to an embodiment, the polymer salt is administered for a sufficient period of time to alleviate the symptoms of Syndrome X or to inhibit the onset of symptoms of Syndrome X.

In a particular embodiment, the polymer salt that is administered includes a reaction product having: (i) at least some of the nitrogen atoms in the repeat units unreacted with the alkylating agent; (ii) less than 10 mol % of the nitrogen atoms in the repeat units reacting with the alkylating agent, forming quaternary ammonium units; and (iii) a fixed positive charge and one or more counterions, and wherein the alkylation of the polymer product is carried out prior to cross-linking.

A method for treating Syndrome X or inhibiting the onset of symptoms of Syndrome X in a patient, according to a particular embodiment includes administering a therapeutically effective amount of poly(allylamine hydrochloride) cross-linked with epichlorohydrin and/or alkylated with 1-bromodecane and (6-bromohexyl)-trimethylammonium bromide, wherein the polyallylamine is administered for a sufficient period of time to alleviate the symptoms of Syndrome X or to inhibit the onset of symptoms of Syndrome X.

In another embodiment, a method for treating the pathologies associated with Syndrome X or inhibiting the onset of symptoms of the pathologies associated with Syndrome X in a patient includes administering to the patient a therapeutically effective amount of the salt of at least one alkylated and cross-linked polymer, or a copolymer thereof, the polymer salt formed as a reaction product of the reaction of one or more polymers, or salts and copolymers thereof, having a repeat unit that is essentially:

where n is a positive integer and each R, independently, is H or a $C_1$–$C_8$ alkyl group; at least one aliphatic alkylating agent; and a cross-linking agent. According to an embodiment, the polymer salt is administered for a sufficient period of time to alleviate the symptoms of the pathologies associated with Syndrome X or to inhibit the onset of symptoms of the pathologies associated with Syndrome X.

In one embodiment, the invention is a method for treating the pathologies associated with Syndrome X or inhibiting the onset of symptoms of the pathologies associated with Syndrome X in a patient, including administering to the patient a therapeutically effective amount of poly(allylamine hydrochloride) cross-linked with epichlorohydrin and alkylated with 1-bromodecane and (6-bromohexyl)-trimethylammonium bromide, wherein the polyallylamine is administered for a sufficient period of time to alleviate the symptoms of the pathologies of Syndrome X or to inhibit the onset of symptoms of the pathologies of Syndrome X.

The method of the invention also includes administration of the polymer salt colesevelam, in combination with an HMG-CoA reductase inhibitor. The combined administration is effective in further lowering serum total-cholesterol and LDL-cholesterol levels beyond that achieved by either agent alone.

Other features and advantages will be apparent from the following description of the preferred embodiments thereof and from the claims.

DETAILED DESCRIPTION OF THE INVENTION

The invention relates to the unexpected discovery that long term administration of certain polyamines, such as colesevelam, raises HDL levels in patients. This effect is relevant in an embodiment that includes the prophylaxis or treatment of Syndrome X and the pathologies associated with Syndrome X, an illness which is a combination of metabolic disorders, and which neither regresses spontaneously nor generally responds with any degree of long term success to conventional forms of treatment.

Figure 1:
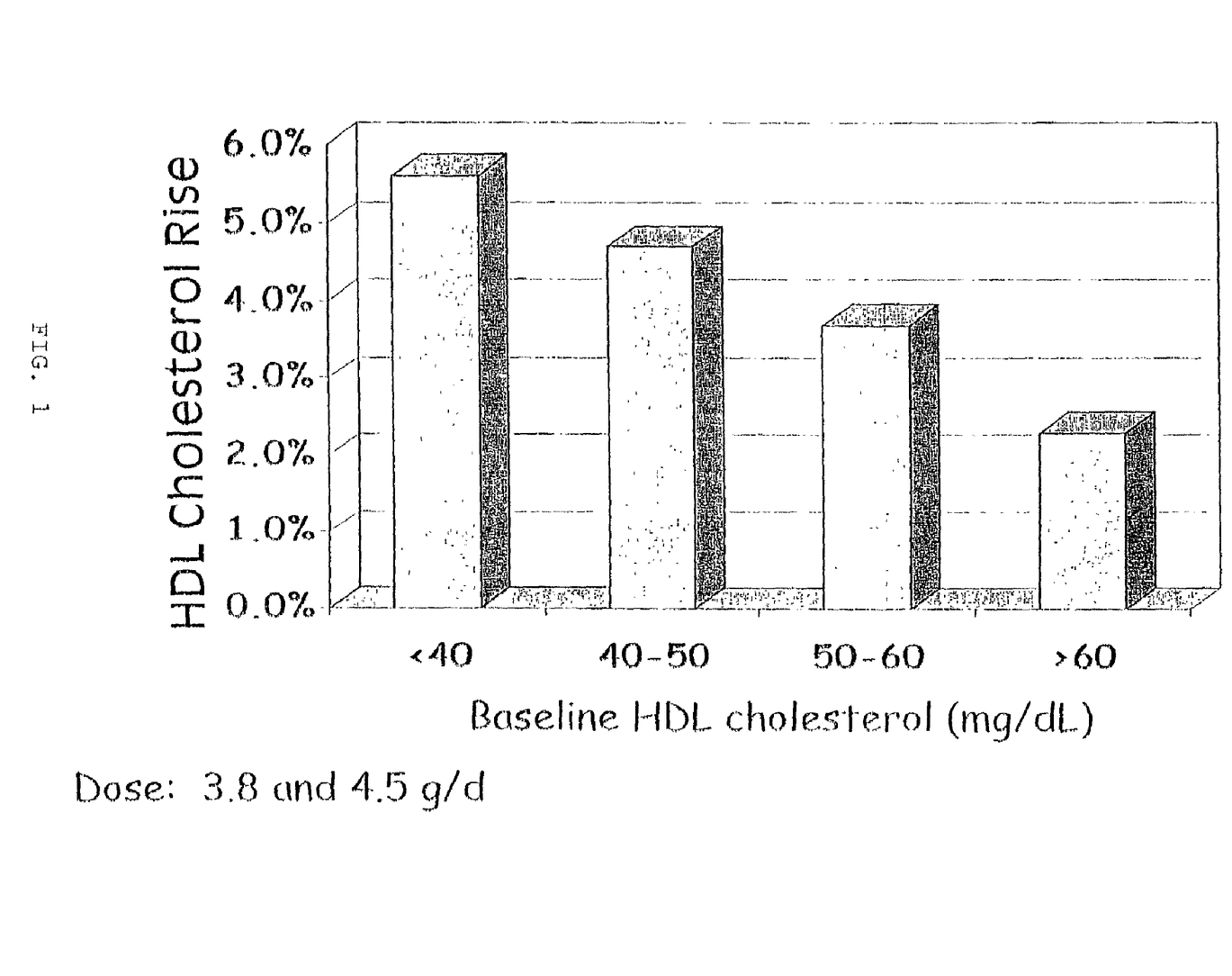
FIG. 1 is a graph showing the percent HDL cholesterol increase versus baseline HDL cholesterol in mg/dL, for a polymer salt dose of 3.8 to 4.5 g/day.

It was also discovered that, in the group of patients treated with one or more polymer salts according to an embodiment (polymer salt dose of 3.8 to 4.5 g/day), those patients having lower initial HDL's tend to have the greatest percent increases in HDL. This effect is illustrated graphically in FIG. 1.

Figure 2:
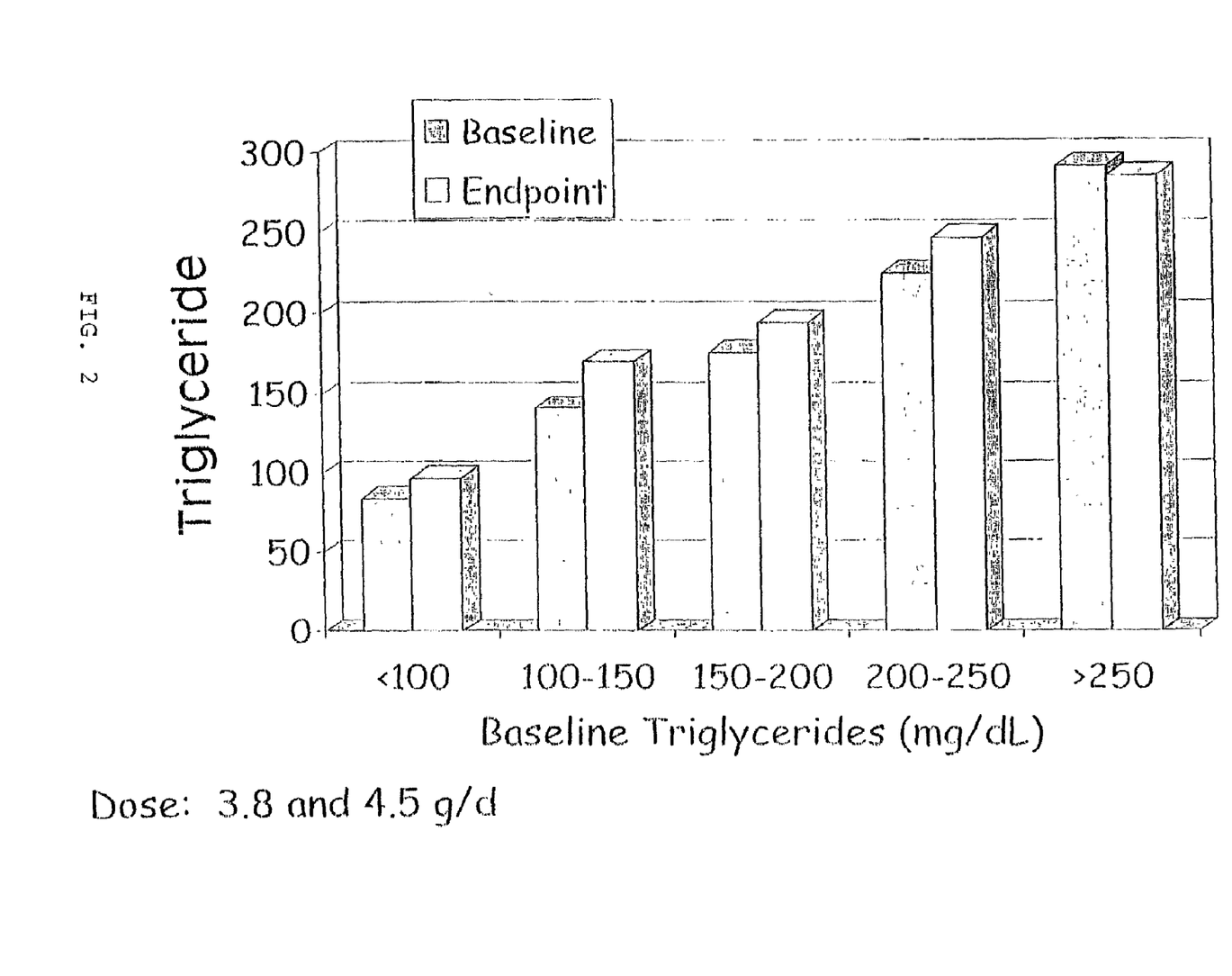
FIG. 2 is a graph showing triglyceride increase as a function of baseline triglycerides (mg/dL), for a polymer salt dose of 3.8 to 4.5 g/day.

It was further discovered that, in the group of patients treated with one or more polymer salts according to an embodiment (polymer salt dose of 3.8 to 4.5 g/day), those patients having relatively higher baseline triglycerides had the smallest increases in triglycerides. This effect is illustrated graphically in FIG. 2.

As described above, the preferred polymers employed in an embodiment of the method of the invention comprise water-insoluble, non-absorbable, preferably cross-linked polyamine polymer salts, such as aliphatic polyamines characterized by one or more hydrophobic substituents and/or one or more quaternary ammonium containing substituents.

In one embodiment, the polymer salt is characterized by 10 or more monomeric units and/or possesses a molecular weight of about 570 or more, preferably about 5,000 daltons or more.

Preferably the polymer salt is non-absorbable in the gastrointestinal tract and/or substantially water-insoluble. The terms "insoluble," "substantially water-insoluble," and grammatical variations thereof, as used herein, refer to a polymer or other substance which does not dissolve in an aqueous-based system, or which dissolves or solubilizes at a slower rate than does a water-soluble substance. Water-insoluble polymers introduced into the gastrointestinal tract are not absorbed systemically, or are absorbed to a lesser extent than are water-soluble polymers.

"Nonabsorbent" or "non-absorbable," as the terms are used herein, means that the polymer or other substance so described does not dissolve in the gastrointestinal tract, or dissolves to a lesser extent than does an absorbent or absorbable substance, or does not erode, degrade, or otherwise break down in vivo to form smaller chemical species by either physical or chemical processes. Therefore, a non-absorbable polymer is not absorbed systemically or is absorbed to a lesser extent than is an absorbable polymer. Accordingly, preferred reaction products of the invention include polymers that are cross-linked. A higher level of cross-linking decreases the water-solubility of the polymers, making them less absorbable, and thus substantially limits the activity of the alkylated, cross-linked polymers to the gastrointestinal tract only. Thus, because a highly cross-linked polymer of the invention is non-absorbable, the potential for undesirable side-effects in the patient is diminished.

"Alkylating agent," as the term is used herein, means a reactant which, when reacted with the cross-linked polymer, causes an alkyl group or derivative thereof (e.g., a substituted alkyl, such as an aralkyl, hydroxyalkyl, alkylammonium salt, alkylamide, or combination thereof) to be covalently bound to one or more of the nitrogen atoms of the polymer.

Suitable substituents for use in an embodiment include quaternary ammonium, amine, alkylamine, dialkylamine, hydroxy, alkoxy, halogen, carboxamide, sulfonamide and carboxylic acid ester, for example.

As described above, in one embodiment of the method, the polymer is administered in the form of a salt. As used herein, the term "salt" means that the nitrogen group in the repeat unit is protonated to create a positively charged nitrogen atom associated with a negatively charged counterion. A preferred polymer is a low salt, such as low chloride, form of polyallylamine where less than 40% of the amine groups are protonated.

The anionic counterions are selected to minimize adverse effects on the patient, as is more particularly described below. In a preferred embodiment, the counterion is selected to have a therapeutic benefit to the patient. Examples of suitable counterions include organic ions, inorganic ions, or a combination thereof, such as halides ($Cl^-$ and $Br^-$), $CH_3OSO_3^-$, $HSO_4^-$, $SO_4^{2-}$, $HCO_3^-$, $CO_3^{2-}$, acetate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. In one embodiment, the counterions are identical. In another embodiment, the counterions are different from each other. For example, a polymer salt according to one embodiment contains two different types of counterions.

Cross-linking

In a preferred embodiment, an amine polymer is cross-linked by means of a multifunctional cross-linking agent. A "multifunctional cross-linking agent," as that phrase is used herein, is a molecule containing two or more functional groups that can react with functional groups such as amine groups on polymers and form intramolecular or intermolecular chemical links between the chains of the polymers.

The polymers are preferably cross-linked prior to alkylation. Because of its high availability and low cost, epichlorohydrin is a preferred cross-linking agent according to an embodiment. Epichlorohydrin is also advantageous for use in an embodiment because of its low molecular weight and its hydrophilic nature, which increases the water-swellability and gel properties of the polyamine.

Other examples of cross-linking agents suitable for use in an embodiment include acryloyl chloride, butanedioldiglycidyl ether, ethanedioldiglycidyl ether, and dimethyl succinate.

The amount of cross-linking agent used in an embodiment is typically between about 0.5% and about 25% (preferably between about 2.5% and about 20%; most preferably between about 1% and about 10%), based upon the combined weight of cross-linking agent and monomer.

Typically, the amount of cross-linking agent that is reacted with the amine polymer is sufficient to cause reaction of between about 0.5 percent and about twenty percent of the amine groups. In a preferred embodiment, between about 0.5 percent and about six percent of the amine groups react with the cross-linking agent.

Cross-linking of the polymer can be achieved by reacting the polymer with a suitable cross-linking agent in an aqueous caustic solution at about 25° C. for a period of about eighteen hours to thereby form a gel. The gel is then combined with water and blended to form a particulate solid. The particulate solid can then be washed with water and dried under suitable conditions, such as a temperature of about 50° C. for a period of about eighteen hours.

Alkylation

Alkylation involves reaction between the nitrogen atoms of the polymer and the alkylating agent (which may contain additional nitrogen atoms, e.g., in the form of amido or ammonium groups). In addition, the nitrogen atoms which do react with the alkylating agent(s) resist multiple alkylation to form quaternary ammonium ions such that less than 10 mol % of the nitrogen atoms have formed quaternary ammonium ions at the conclusion of alkylation.

The alkylating agents according to an embodiment are selected to provide hydrophobic regions and hydrophilic regions. In preferred embodiments, alkylating agents have the formula RX where R is a C1–C20 alkyl (preferably C4–C20), C1–C20 hydroxy-alkyl (preferably C4–C20 hydroxyalkyl), C7–C20 aralkyl, C1–C20 alkylammonium (preferably C4–C20 alkyl ammonium), or C1–C20 alkylamido (preferably C4–C20 alkyl amido) group and X includes one or more electrophilic leaving groups. As the phrase is used herein, "electrophilic leaving group" means a group that is displaced, during the alkylation reaction, by a nitrogen atom in the cross-linked polymer. Examples of preferred leaving groups include halide, epoxy, tosylate, and mesylate group. In the case of, e.g., epoxy groups, the alkylation reaction according to an embodiment causes opening of the three-membered epoxy ring.

Examples of alkylating agents according to preferred embodiments include a C1–C20 alkyl halide (e.g., an n-butyl halide, n-hexyl halide, n-octyl halide, n-decyl halide, n-dodecyl halide, n-tetradecyl halide, n-octadecyl halide, and combinations thereof); a C1–C20 dihaloalkane (e.g., a 1,10-dihalodecane); a C1–C20 hydroxyalkyl halide (e.g., an 11-halo-1-undecanol); a C1–C20 aralkyl halide (e.g., a benzyl halide); a C1–C20 alkyl halide ammonium salt (e.g., a (4-halobutyl) trimethylammonium salt, (6-halohexyl)trimethylammonium salt, (8-halooctyl)trimethylammonium salt, (10-halodecyl)trimethylammonium salt, (12-halododecyl)-trimethylammonium salts and combinations thereof); a C1–C20 alkyl epoxy ammonium salt (e.g., a (glycidylpropyl)-trimethylammonium salt); and a C1–C20 epoxy alkylamide (e.g., an N-(2,3-epoxypropane)butyramide, N-(2,3-epoxypropane) hexanamide, and combinations thereof).

In a preferred embodiment, the polymer is reacted with at least two alkylating agents, added simultaneously or sequentially to the polymer. In one preferred embodiment, for example, one of the alkylating agents has the formula RX where R is a C1–C20 alkyl group and X includes one or more electrophilic leaving groups (e.g., an alkyl halide), and the other alkylating agent has the formula R'X where R' is a C1–C20 alkyl ammonium group and X includes one or more electrophilic leaving groups (e.g., an alkyl halide ammonium salt).

In a particular embodiment, one of the alkylating agents has the formula RX and is a C10 alkyl halide, and the other alkylating agent has the formula R'X and is a C6 alkyl halide trimethyl ammonium salt.

In another preferred embodiment, one of the alkylating agents has the formula RX where R is a C1–C20 alkyl group and X includes one or more electrophilic leaving groups (e.g., an alkyl halide), and the other alkylating agent has the formula R'X where R' is a C1–C20 hydroxyalkyl group and X includes one or more electrophilic leaving groups (e.g., a hydroxy alkyl halide).

In another preferred embodiment, one of the alkylating agents is a C1–C20 dihaloalkane and the other alkylating agent is a C1–C20 alkylammonium salt.

The reaction products according to an embodiment are cations having fixed positive charges; these cations attract and acquire negatively charged counterions upon ingestion. According to another embodiment, the reaction product is provided with one or more counterions, and is essentially neutral in charge. The counterions, whether acquired when ingested or provided in the product-forming reaction, can be exchanged with ions of bile salts. Examples of counterions suitable for use in an embodiment are provided above. In one embodiment of the method, the polymer salt administered contains two different types of counterions, both of which are exchanged for bile salts. The result of the exchange of counterions for ions of bile salts is that, during long term administration of the polymer salt, the bile salts are removed from the gastrointestinal tract. In another embodiment, more than one reaction product, each having different counterions associated with the fixed charges, are administered.

In another embodiment the reaction products have the capability of becoming positively charged upon ingestion at physiological pH. The charged ions, upon their formation, attract and acquire negatively charged counterions. According to an embodiment, the acquired counterions are exchanged with ions of bile salts, thereby removing the bile salts from the gastrointestinal tract.

The amine polymer is typically alkylated according to a method of the invention by combining the polymer with the alkylating agents in an organic solvent. A preferred organic solvent for use in an embodiment is methanol. Examples of other organic solvents suitable for use in an embodiment include ethanal, isopropanol, acetonitrile, dimethylformamide (DMF) and dimethyl sulfoxide (DMSO).

In one embodiment, the alkylating agent is added to the cross-linked polymer at a molar ratio between about 0.05:1 and about 4:1. According to an embodiment, the amount of first alkylating agent combined with the amine polymer is generally sufficient to cause reaction of the first alkylating agent with between about 5 percent and about 75 percent of amine groups on the amine polymer that are available for reaction. The amount of second alkylating agent combined with the amine polymer and solution is generally sufficient to cause reaction of the second alkylating agent with between about 5 percent and about 75 percent of the amine groups available for reaction on the amine polymer.

In one embodiment, the reaction mixture is heated over a period of about forty minutes to a temperature of about 65° C., with stirring. According to a typical embodiment, an aqueous sodium hydroxide solution is continuously added during the reaction period. In a preferred embodiment, the reaction is carried out at a temperature of about 65° C. for a period of about eighteen hours, followed by gradually cooling the mixture to a room temperature of about 25° C. over a period of about four hours. According to a method of the invention, the resulting reaction product is then filtered, re-suspended in methanol, filtered again, washed with a suitable aqueous solution (eg., two molar sodium chloride), and then washed with de-ionized water. According to an embodiment, the resultant solid product is then dried under suitable conditions, such as at a temperature of about 60° C. in an air-drying oven. The dried solid can then be subsequently processed. In a preferred embodiment, the solid is ground and passed through an 80 mesh sieve.

The following are examples of polymers of the invention that are not intended to limit the scope of the invention in any way.

EXAMPLES OF SOME POLYMER SALTS OF THE INVENTION

One example of a preferred polymer salt used in a method of the invention is the reaction product of: (a) a polymer characterized by a repeat unit having the formula (3)

or a salt or copolymer thereof; wherein n is a positive integer, x is zero or an integer between about 1 to 4 (preferably 0 or 1), and each R, independently, is H or a $C_1$-$C_8$ alkyl group; and (b) at least one aliphatic alkylating agent; and (c) a cross-linking agent, wherein said reaction product has: (i) at least some of the nitrogen atoms in said repeat units unreacted with said alkylating agent; (ii) less than 10 mol % of the nitrogen atoms in said repeat units reacting with said alkylating agent forming quaternary ammonium units; and (iii) a fixed positive charge and one or more counterions and wherein the polymer is alkylated prior to cross-linking.

A second example of a preferred polymer is characterized by a repeat unit having the formula (4)

or a salt or copolymer thereof.

A third example of a preferred polymer is characterized by a repeat unit having the formula (5)

or a salt or copolymer thereof.

Preferred polymer salts comprise aliphatic amine polymers including poly(allylamine), alkylated poly(allylamine), poly(vinylamine), poly(diallylamine) and poly(ethyleneimine) or a salt thereof with a pharmaceutically acceptable acid. The aliphatic amine polymer is optionally substituted at one or more nitrogen atoms with an alkyl group or a substituted alkyl group such as a trialkylammoniumalkyl group. The aliphatic amine polymer can optionally be cross-linked, for example via a multifunctional monomer or a bridging group which connects two amino nitrogen atoms from two different polymer strands. In a preferred embodiment, the aliphatic amine polymer resin is hydrated.

In a preferred embodiment, the polymer is a poly(allylamine hydrochloride) crosslinked with epichorohydrin and alkylated with 1-bromodecane and (6-bromohexyl)-trimethylammonium bromide (U.S. Pat. Nos. 5,607,669 and 5,679,717), also referred to as colesevelam hydrochloride or colesevelam and marketed in the United States as WelChol™(GelTex Pharmaceuticals, Inc., Waltham, Mass.). In another embodiment, an epichorohydrin-cross-linked poly(allylamine hydrochloride) resin (U.S. Pat. Nos. 5,496, 545 and 5,667,775), also referred to as sevelamer hydrochloride or sevelamer and marketed as Renagel® (GelTex Pharmaceuticals, Inc.), can be used. The compositions are non-toxic and stable when ingested in therapeutically effective amounts.

The aliphatic amine polymer resin can be any of the aliphatic amine resins that increase HDL and decrease LDL upon long term administration. Suitable amine resins for use in the method of the invention include those described in U.S. Pat. Nos. 5,496,545; 5,667,775; 5,624,963; 5,703,188; 5,679,717; 5,693,675; 5,607,669; 5,618,530; 5,487,888; and 5,702,696, the teachings of each of which are hereby incorporated herein by reference in their entireties. Other suitable aliphatic amine polymers are disclosed in U.S. Pat. Nos. 6,034,129 and in U.S. Ser. No. 08/979,096, the teachings of each of which are hereby incorporated herein by reference in their entireties.

Additional polymers which can be used in the present invention are described in U.S. Pat. Nos.: 6,248,318; 6,225, 355; 6,203,785; 6,190,649; 6,177,478; 6,129,910; 6,083, 497; 6,083,495; 6,066,678; 6,060,517; 5,919,832; 5,981, 693; 5,969,090; 5,929,184; 5,925,379; 5,917,007; 5,900, 475; and 5,840,766, and pending U.S. patent application Ser. Nos.: 09/203,319; 09/165,386; and 09/165,386; the teachings of which are incorporated herein by reference in their entireties.

In a particularly preferred embodiment of the invention, the amine polymer is a cross-linked poly(allylamine), wherein the first substituent includes a hydrophobic decyl moiety, and the second amine substituent includes a hexyltrimethylammonium. Further, the particularly preferred cross-linked poly(allylamine) is cross-linked by epichlorohydrin that is present in a range of between about two and about six percent of the amines available for reaction with the epichlorohydrin.

Administration

To achieve the improvements described herein, the present invention provides for a method of administering the polymers to the gastrointestinal tract. Compositions of the invention can be administered to the gastrointestinal tract of an individual in a variety of ways. In a preferred embodiment, the compositions of the present invention are administered orally. In another embodiment, the compositions of the invention are administered by surgical insertion into the gastrointestinal tract. The administration according to another embodiment is an administration that is a combination of two or more routes of administration.

While a composition of the invention for use in treating Syndrome X or inhibiting the onset of symptoms of Syndrome X may be administered in the form of the polymer compound itself, including a physiologically acceptable salt thereof, in a particular embodiment the polymer is administered in a pharmaceutical composition together with one or more adjuvants, excipients, carriers and/or diluents.

Therefore, in another embodiment, the present invention also relates to pharmaceutical compositions which include a suitable pharmaceutical carrier and at least one alkylated and cross-linked polymer or copolymer of the invention. Any of the compositions of the present invention described herein may be administered with a suitable pharmaceutical carrier, the choice of which depends on the route of administration and the condition of the patient.

The terms "suitable pharmaceutical carrier," "pharmaceutically acceptable carrier," and grammatical variations thereof, as they refer to compositions, carriers, diluents and reagents, are used herein interchangeably. As the terms are used herein, "suitable pharmaceutical carrier" and "pharmaceutically acceptable carrier" refer to non-toxic materials that do not interfere with the effectiveness of the biological activity of active ingredients, and represent that the materials are capable of administration to or upon a vertebrate with a minimum of undesirable physiological effects such as nausea, dizziness, gastric upset and the like.

The preparation of a pharmacological composition that contains active ingredients dissolved or dispersed therein is well understood in the art and need not be limited based on formulation. Liquid preparations include solutions, suspensions, colloids, hydrogels, and emulsions, for example, water or water-propylene glycol mixtures. Solid forms suitable for forming into tablets, filling capsules, or suspending in liquid prior to use can also be prepared. The preparation can also be emulsified.

A polymer salt of the invention can be mixed with excipients which are pharmaceutically acceptable and compatible with the polymer salt, and in amounts suitable for use in the therapeutic methods described herein. Suitable excipients include, for example, water, saline, dextrose, glycerol, ethanol or the like and combinations thereof. The tablets, pills, capsules, and the like containing a polymer salt of the invention may also contain excipients such as a dicalcium phosphate; a disintegrating agent such as corn starch, potato starch, alginic acid; a lubricant such as magnesium stearate; and a sweetening agent such as sucrose, lactose or saccharin.

In one embodiment a composition of the invention contains a binder such as gum tragacanth, acacia, corn starch or gelatin. Various other materials may be present as coating or to modify the physical form of the dosage unit. For instance, a tablet may be coated with shellac, sugar or both. A syrup or elixir may contain, in addition to the polymer salt, sucrose as a sweetening agent, methylparabens or propylparabens as a preservative, a dye and a flavoring such as cherry or orange flavor. For example, tablet formulations suitable for use in the present invention are described in U.S. patent application No. 09/875,275, the teachings of which are incorporated herein by reference.

In addition, if desired, the composition can contain minor amounts of auxiliary substances such as pH buffering agents and the like which enhance the effectiveness of the active ingredient. Details on techniques for formulation and administration may be found in the latest edition of *Remington's Pharmaceutical Sciences* (Maack Publishing Co., Easton, Pa.).

Therapeutically Effective Amount and Dosage

A polymer of the invention is administered to a patient in a therapeutically effective amount. As used herein, the terms "therapeutically effective amount" and "therapeutically effective dose" have the same meaning and refer to the amount of an active agent, for example, a therapeutically effective substance, such as a polymer of the invention, required to be administered in order to induce a desired result in the patient. That result may be alleviation or amelioration (complete or partial) of the symptoms of Syndrome X or of the condition of the patient in need of treatment, any other desired improvement in the patient's symptoms, disease or condition, or prophylaxis or delay in the onset of symptoms of Syndrome X.

As used herein, the term "therapeutically effective amount" may also refer to the quantity of active agent or therapeutically effective substance, such as an amine polymer of the invention, the administration of which results in improvement in the patient's symptoms, disease, or condition, where little or no improvement would occur in the absence of the active agent. Typically, the polymer is administered for a sufficient period of time to achieve the desired therapeutic effect.

Therapeutic efficacy may be determined by using standard pharmacological procedures in experimental animals.

For example, the term "therapeutically effective amount" is intended to mean an amount of a composition of the invention that will elevate an individual's plasma HDL level and decrease the LDL level in comparison to the level prior to administration of the composition. Measurement of plasma HDL and LDL can be performed using any medically acceptable procedures known to those of skill in the medical arts, including assay kits designed for use directly by consumers.

In accordance with this invention, an HDL-raising amount of a polymer salt of the invention can be used for the preparation of a medicament useful for raising the plasma level of high density lipoprotein in mammals, particularly in humans. In a preferred embodiment, an HDL-raising amount of a polymer salt can be used for treating patients with Syndrome X. According to the method of the invention, an HDL-raising amount of a polymer salt can also be administered for treating the symptoms of the pathologies associated with Syndrome X, and for inhibiting the onset of the symptoms of the pathologies associated with Syndrome X.

The dosage regimen of cross-linked polyamines of the present invention is selected in accordance with a variety of factors including type, species, age weight, sex and medical condition of the patient; the severity of the condition to be treated; the route of administration; the renal and hepatic function of the patient; and the particular cross-linked polyamine agent employed. Consideration of these and other relevant factors are well within the purview of the ordinarily skilled clinician for determination of an appropriate therapeutic regimen of cross-linked polyamines of the invention to prevent, attenuate or arrest the progress of the condition.

Generally, a therapeutic amount of a polymer salt of the invention is in the range of between about 0.1 gram/day and about 10 grams/day. In one embodiment of the method of the invention, a polymer salt is administered to the gastrointestinal tract in a dosage of between about 1.5 g per day and about 4.5 g per day. In another embodiment, a polymer salt is administered to the gastrointestinal tract in a dosage of between about 2.3 g per day and about 3.8 g per day. In a preferred embodiment, the daily dose is about 3.8 grams/day. This dosage regimen may be adjusted to provide the optimal therapeutic response. In one embodiment of the method of the invention, the polymer salt is administered with one or more meals.

In embodiments of the above-described methods, the polyamine salts of the invention may be administered to the gastrointestinal tract either alone or in combination with one or more additional bioactive agents, or therapeutically effective substances. As used herein, the terms "therapeutically effective substance" or "therapeutic substance" include:

(i) Compounds and compositions recognized in the official United States Pharmacopoeia, the official Homeopathic Pharmacopoeia of the United States, or the official National Formulary, or any supplement of any of them;

(ii) Compounds and compositions intended for use in the diagnosis, cure, mitigation, treatment, or prevention of disease in man or other animals; and (iii) Compounds and compositions (other than food) intended to affect the structure or any function of the body of man or other animals.

Examples of therapeutically effective substances suitable for use in a method of the invention include enzyme inhibitors, for example, a cholesterol biosynthesis inhibitor, such as an inhibitor of HMG CoA reductase.

Combination therapy includes administration of a single pharmaceutical dosage formulation which contains at least one polyamine of the invention and one or more additional bioactive agents, as well as administration of the polyamine in one pharmaceutical dosage formulation and administration of the bioactive agent in its own separate pharmaceutical dosage formulation. For example, in one embodiment, a polyamine of the invention and an enzyme inhibitor such as an HMG-CoA reductase inhibitor is administered to the patient together in a single oral dosage composition such as a tablet or capsule. In an alternate embodiment, each agent is administered in a separate oral dosage formulation. Where separate dosage formulations are used, the polyamine and one or more additional bioactive agents can be administered at essentially the same time, i.e., concurrently or at separately staggered times, i.e., sequentially; combination therapy is understood to include all these regimens.

For example, the polyamine salt may be administered in combination with one or more of the following bioactive agents: an antihyperlipidemic agent, such as LXR agonists (see WO 01/03705); a plasma HDL-raising agent; an antihypercholesterolemic agent, such as cholesterol biosynthesis inhibitor, for example an HMG-CoA reductase inhibitor (such as a statin), an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor, such as melinamide; probucol; nicotinic acid and the salts thereof and niacinamide; a cholesterol absorption inhibitor such as beta-sitosterol; a bile acid sequestrant anion exchange resin, such as cholestyramine, colestipol or a dialkylaminoalkyl derivatives of a cross-linked dextran; and LDL (low density lipoprotein) receptor inducer; fibrates such as clofibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); anti-oxidant vitamins, such as vitamins C and E, and beta carotene: a beta-blocker; and angiotensin II antagonist converting enzyeme inhibitor; and a platelet aggregation inhibitor, such as fibrinogen receptor antagonists (i.e., glycoprotein IIb/IIIa fibrinogen receptor antagonists) and aspirin.

As noted above, the polyamine salt can be administered in combination with more than one additional bioactive agent. For example, in one embodiment of the method, a combination of polyamine salt with an HMG-CoA reductase inhibitor and aspirin, or a combination of polyamine salt with an HMG-CoA reductase inhibitor and a beta blocker is administered.

The term HMG-CoA reductase inhibitor is intended to include all pharmaceutically acceptable salt, ester, free acid and lactone forms of compounds which have HMG-CoA reductase inhibitory activity. Therefore, the use of such salts, esters, free acids and lactone forms are included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131, the teachings of which are incorporated herein by reference. Examples of suitable HMG-CoA reductase inhibitors include, but are not limited to, resistin (see WO 00/64920); lovastatin (MEVACOR®; see, U.S. Pat. No. 4,231,938); simvastatin (ZOCOR®; see U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see U.S. Pat. No. 5,273,995) and rivastatin (also known as cerivastatin; see U.S. Pat. No. 5,177,080). The structural formulas of these and additional HMG-CoA reductase inhibitors that can be used in the methods of the present invention are described in M. Yalpani, "Cholesterol Lowering Drugs," *Chemistry and Invention*, pp. 85–89, at p. 87 (Feb. 5, 1996). In presently preferred embodiments, the HMG-CoA reductase inhibitor is selected from lovastatin and simvastatin.

Dosage information for HMG-CoA reductase inhibitors, several of which are marketed in the U.S., is well known in the art. In one embodiment of the method of the invention, the daily dosage amounts of an HMG-CoA reductase inhibitor are the same or similar to those amounts which are employed for anti-hypercholesterolemic treatment. For example, see "Hypolipidemics," *Physicians' Desk Reference* 50$^{th}$ ed., (Medical Economics Co.): 216 (1996). Preferably, the oral dosage amount of HMG-CoA reductase inhibitor is between about 1 mg/day and about 200 mg/day, and more preferably, between about 5 mg/day and about 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amounts for simvastatin may be selected from 5 mg, 10 mg, 20 mg, 40 mg, 80 mg and 160 mg; for lovastatin, 10 mg, 20 mg, 40 mg and 80 mg; for fluvastatin sodium, 20 mg, 40 mg and 80 mg; and for pravastatin sodium, 10 mg, 20 mg and 40 mg. The daily dosage amount for atorvastatin calcium may be in the range of between about 1 mg to about 160 mg and, more particularly, between about 5 mg and about 80 mg. Oral administration may be in single or divided doses of two, three, or four times daily, although a single daily dose of the HMG-CoA reductase inhibitor is preferred.

The invention is described in more detail in the following examples. These examples are provided by way of illustration and are not intended to limit the invention in any way.

Exemplification

EXAMPLE 1

Preparation of Poly(allylamine) Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 g) was added dropwise with stirring while maintaining the reaction temperature between about 5° C. and about 10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis(amidinopropane) dihydrochloride (0.5 g) suspended in 11 mL of water was then added. The resulting reaction mixture was heated to about 50° C. under a nitrogen atmosphere with stirring for 24 hours. Additional azobis(amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 g of poly(allylamine) hydrochloride as a granular white solid.

EXAMPLE 2

Preparation of Poly(allylamine) Hydrochloride Cross-linked with Epichlorohydrin To a 5 gallon vessel was added poly(allylamine) hydrochloride prepared as described in Example 1 (1 kg) and water (4 L). The mixture was stirred to dissolve the hydrochloride and the pH was adjusted by adding solid NaOH (284 g). The resulting solution was cooled to room temperature, after which epichlorohydrin cross-linking agent (50 mL) was added all at once with stirring. The resulting mixture was stirred gently until it gelled (about 35 minutes). The cross-linking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross-linked polymer as a granular, brittle, white solid.

EXAMPLE 3

Alkylation of Poly(allylamine) Cross-linked with epichlorohydrin with (6-Bromohexyl)trimethylammonium bromide and 1-bromodecane alkylating Agent To a 12-1 round bottom flask equipped with a mechanical stirrer, a thermometer, and a condenser was added methanol (5 L) and sodium hydroxide (133.7 g). The mixture was stirred until the solid dissolved. Cross-linked poly(allylamine) (297 g, ground to –80 mesh size) was added along with additional methanol (3 L). (6-Bromohexyl) trimethylammonium bromide (522.1 g) and 1-bromodecane (311.7 g) were added and the mixture heated to 65° C. with stirring. After 18 hours at 65° C. the mixture was allowed to cool to room temperature. The solid was filtered off and rinsed by suspending, stirring for 30 minutes, and filtering off the solid from: methanol, 12 L; methanol, 12 L; 2 M aqueous NaCl, 22 L; 2 M aqueous NaCl, 22 L; deionized water, 22 L; deionized water, 22 L; deionized water, 22 L and isopropanol, 22 L. The solid was dried in a vacuum oven at 50° C. to yield 505.1 g of off-white colored solid. The solid was then ground to pass through an 80 mesh sieve.

EXAMPLE 4

Preparation of Poly (vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirrer. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and the mixture stirred for a few minutes, after which the solid was filtered off and discarded. The acetone was cooled to 0° C. and solid was filtered off. This solid was rinsed in 500 mL acetone and air dried 18 hours to yield 31.5 g of ethylidenebisacetamide.

The next step involved the preparation of vinylacetamide from ethylidenebisacetamide. Ethylidenebisacetamide (31.05 g), calcium carbonate (2 g) and celite 541 (2 g) were placed in a 500 mL three neck flask fitted with a thermometer, a mechanical stirrer, and a distilling heat atop a Vigreaux column. The mixture was vacuum distilled at 24 mm Hg by heating the pot to 180–225° C. Only a single fraction was collected (10.8 g) which contained a large portion of acetamide in addition to the product (determined by NMR). This solid product was dissolved in isopropanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine as follows).

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 cm-1) remained and that not much amine (1606 cm-1) was formed. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

EXAMPLE 5

A Novel, Highly Potent, Polymeric Bile Acid Sequestrant Significantly Lowers LDL Cholesterol WelChol™ contains colesevelam hydrochloride (hereafter referred to as colesevelam), a non-absorbed, polymeric, lipid-lowering agent intended for oral administration. Colesevelam is poly(allylamine hydrochloride) cross-linked with epichlorohydrin and alkylated with 1-bromodecane and (6-bromohexyl)-trimethylammonium bromide. Colesevelam blocks the enterohepatic circulation of bile acids, thereby upregulating hepatic cholesterol 7α-hydroxylase and increasing conversion of cholesterol into bile acids. Bile acid sequestrants decrease the risk of cardiac events, but have low compliance rates. In this randomized, double-blind, placebo-controlled 6 month dose ranging study in patients with type IIa hypercholesterolemia (LDL cholesterol 130–220 mg/dL, mean baseline 158 mg/dL), an 8 week National Cholesterol Education Program (NCEP) Step I diet preceded 24 weeks of treatment in the "Intent-To-Treat" (ITT) population.

Maximum LDL-C reduction occurred by the second week of treatment and was maintained throughout the study. As shown in Table 1, colesevelam administered at 4.5 g/day lowered median LDL-C by 20%. All treatment groups had small but significant increases in HDL-C.

TABLE 1

Percent change in Fasting Plasma Lipid Parameters (ITT Population)

| Dose | n | LDL-C mean | Total-C mean | HDL-C mean | TG median |
|---|---|---|---|---|---|
| placebo | 88 | 0 | 1 | −1 | 5 |
| colesevelam 2.3 g | 99 | −9* | −4* | 3* | 9† |
| colesevelam 3.0 g | 90 | −12* | −6* | 4* | 5† |
| colesevelam 3.8 g | 95 | −15* | −7* | 3* | 10* |
| colesevelam 4.5 g | 94 | −18* | −10* | 3* | 10† |

†p-value < 0.05; *p-value < 0.001 within group change

The overall incidence of side effects was comparable between treatment and placebo groups. Colesevelam was safe and effective mono therapy for type IIa hypercholesterolemia. Compared to historical data with other bile acid sequestrants, colesevelam hydrochloride was 4–6 times more potent, and the incidence of treatment related gastrointestinal side effects was not statistically different from placebo.

EXAMPLE 6

An Extended Use Study of Colesevelam in Patients with Primary Hypercholesterolemia The objective of this study was to expose a sufficiently large group of patients to colesevelam to determine long-term safety and efficacy. Of particular interest was the question of whether or not colesevelam would interfere with the absorption of fat-soluble vitamins with long-term dosing. This study was conducted at 10 sites.

Study Design

| Diet | Treatment | Washout |
|---|---|---|
| (4 weeks) | (50 weeks) ↑↑↑↑↑↑↑↑↑↑ Dose Titrations | (2 weeks) |

This was an open-label extension study enrolling patients from three groups for up to 50 weeks of treatment. Following screening, patients with mild to moderate hypercholesteremia were entered into the National Cholesterol Education Program (NCEP) Step 1 diet for 4 weeks. Those patients who met the entrance criteria were enrolled into the 50-week treatment period. Patients were to take 2 to 5 capsules, each containing 375 mg of colesevelam, twice per day with meals. Patients began dosing at 2 capsules with meals twice a day at Day 0. The dose was to be titrated to achieve a 15–30% reduction in LDL cholesterol from the baseline value. Increases could occur in one capsule twice per day increments, at scheduled visits beginning at the Week 2 visit, based on rapid lipid measurements and clinical judgment. If the maximal dose of colesevelam alone did not sufficiently lower LDL cholesterol, the investigator was allowed to add another lipid-lowering medication (either nicotinic acid or an HMG-CoA reductase inhibitor). A 2-week washout period followed the 50-week treatment period. Safety and efficacy data were to be collected at each visit.

The primary efficacy measure was the change and percent change in LDL cholesterol from baseline to the end of the treatment period. Safety was evaluated by assessing the occurrence and frequency of adverse events, changes in physical examinations, vital signs, and laboratory values. Two-hundred seventy two (272) patients were screened for this study, 260 patients were randomized, and 186 (72%) completed the study.

All laboratory analyses were based on the ITT population. In the final study interval, Weeks 42 to 50, only 50% of patients were prescribed the maximum colesevelam dose allowed by the protocol of 3.8 grams (g) per day. A retrospective secondary analysis of the data for patients who were prescribed 3.8 g per day in the final study interval was also conducted. Therefore, the results are presented for both the ITT population and the 3.8 g per day population. No adjustments were made for non-compliance with the prescribed treatment. A post hoc analysis of the "Completer population," those patients who were treated for the entire 50 weeks of the study, was performed to assess more accurately the results attainable in patients on long-term therapy with colesevelam.

Two study conventions were used for analyses in this study. The first and primary analysis convention was the "All Study Visits" convention that included all blood samples collected during the study, whether or not the patient was taking colesevelam alone or colesevelam in combination with an HMG-CoA reductase inhibitor. The secondary analysis convention was the "Colesevelam-Only Visits" convention which included blood samples collected during the period that the patient was taking colesevelam alone.

The mean and median change and percent change in LDL cholesterol from baseline to endpoint were statistically significant for both the ITT patients and those patients who were titrated to 3.8 g of colesevelam. As this was principally a safety study, and not an efficacy study, all laboratory analyses were based on the safety population with no adjustment made for non-compliance with the prescribed treatment. The mean change in LDL cholesterol was −22 mg/dL for the ITT patients and −25 mg/dL for the patients titrated to 3.8 g per day. The mean prescribed colesevelam dose over the duration of the study was 2.8 g per day. The mean prescribed dose in the final month of the study was 3.3 g per day. An 11% LDL cholesterol reduction was achieved with colesevelam alone at this 3.3 g mean dose. In the completer population the mean baseline to endpoint reduction in LDL cholesterol was 12% for the "Colesevelam Only Visits" convention. The median change was similar. These results are summarized in Table 2 and Table 3.

TABLE 2

Mean Reduction in LDL Cholesterol (Colesevelam Only)

| GROUP | N | Baseline (MG/DL) | Endpoint (MG/DL) | Change (MG/DL) | P-Value | Percent Change | P-Value |
|---|---|---|---|---|---|---|---|
| ITT Patients | 253 | 186 | 164 | −22 | <0.0001 | −11 | <0.0001 |
| 3.8 g. Patients | 97 | 186 | 161 | −25 | <0.0001 | −13 | <0.0001 | p-value obtained from t-test

TABLE 3

Median Reduction in LDL Cholesterol (Colesevelam Only)

| GROUP | N | Baseline (MG/DL) | Endpoint (MG/DL) | Change (MG/DL) | P-Value | Percent Change | P-Value |
|---|---|---|---|---|---|---|---|
| ITT Patients | 253 | 184 | 162 | −20 | <0.0001 | −12 | <0.0001 |
| 3.8 g. Patients | 97 | 183 | 160 | −26 | <0.0001 | −13 | <0.0001 | p-value obtained from t-test

The mean change and the mean percent change in total cholesterol from baseline to endpoint were statistically significant for both the ITT patients and those patients who were titrated to 3.8 g of colesevelam. The mean change in total cholesterol was −12 mg/dL for the ITT patients and −13 mg/dL for the patients titrated to 3.8 g colesevelam per day. These results are summarized in Table 4.

TABLE 4

Mean Reduction in LDL Cholesterol (colesevelam only)

| GROUP | N | Baseline (MG/DL) | Endpoint (MG/DL) | Change (MG/DL) | P-Value | Percent Change | P-Value |
|---|---|---|---|---|---|---|---|
| ITT Patients | 255 | 270 | 258 | −12 | <0.0001 | −4 | <0.0001 |
| 3.8 g. Patients | 98 | 270 | 257 | −23 | <0.0001 | −5 | <0.0001 | p-value obtained from t-test

The median change and the median percent change in HDL cholesterol from baseline to endpoint were statistically significant for both the ITT patients and those patients who were titrated to 3.8 grams of colesevelam. The median change in HDL cholesterol was 5 mg/dL for the ITT patients and 6 mg/dL for the patients titrated to 3.8 grams of colesevelam. These results are summarized in Table 5.

TABLE 5

Median Increases in HIDL Cholesterol (Colesevelam Only)

| GROUP | N | Baseline (MG/DL) | Endpoint (MG/DL) | Change (MG/DL) | P-Value | Percent Change | P-Value |
|---|---|---|---|---|---|---|---|
| ITT Patients | 255 | 50 | 54 | 5 | <0.0001 | 11 | <0.0001 |
| 3.8 g. Patients | 98 | 270 | 257 | 6 | <0.0001 | 13 | <0.0001 | p-value obtained from Wilcoxon Signed-Rank test

The median change and the median percent change in triglycerides from baseline to endpoint were statistically significant for both the ITT patients and those patients who were titrated to 3.8 grams of colesevelam. The median change in triglycerides was 13 mg/dL for the ITT patients and 18 mg/dL for those patients on 3.8 grams of colesevelam. These results are summarized in Table 6.

TABLE 6

Median Increases in Triglycerides

| GROUP | N | Baseline (MG/DL) | Endpoint (MG/DL) | Change (MG/DL) | P-Value | Percent Change | P-Value |
|---|---|---|---|---|---|---|---|
| ITT Patients | 255 | 146 | 165 | 13 | <0.0001 | 10 | <0.0001 |
| 3.8 g. Patients | 98 | 140 | 156 | 8 | <0.0001 | 12 | <0.0001 | p-value obtained from Wilcoxon Signed-Rank test

EXAMPLE 7

Combination Therapy with HMG-CoA Reductase Inhibitors

Thirty-eight (38) patients were treated concomitantly with colesevelam and an HMG-CoA reductase inhibitor at the discretion of their physicians. The mean duration of exposure to combination therapy was 142 days. An analysis of these 38 patients demonstrated statistically significant reductions in LDL and total cholesterol, and a statistically significant increase in HDL cholesterol. A small decrease in triglycerides was not statistically significant. The mean percent reduction in LDL cholesterol was −34% (median −36%) and in total cholesterol was −22%, with p<0.0001 for each of these parameters. The median percent increase in HDL cholesterol was 19% (p<0.0001). The median percent decrease in triglyceride was −3% (p=0.2542). These data demonstrate that combination therapy with colesevelam and HMG-CoA reductase inhibitors over an extended period of time results in excellent long-term reductions in LDL and total cholesterol, and an increase in HDL cholesterol.

Clinical Pharmacology: Mechanism of Action

The mechanism of action for the lipid-lowering activity of colesevelam, the active pharmaceutical ingredient in WelChol™, has been evaluated in various in vitro and in vivo studies. These studies have demonstrated that colesevelam binds bile acids, including glycocholic acid, the major bile acid in humans.

Cholesterol is the sole precursor of bile acids. During normal digestion, bile acids are secreted into the intestine. A major portion of bile acids are then absorbed from the intestinal tract and returned to the liver via the enterohepatic circulation.

Colesevelam is a non-absorbed, lipid-lowering polymer that binds bile acids in the intestine, impeding their reabsorption. As the bile acid pool becomes depleted, the hepatic enzyme, cholesterol 7-α-hydroxylase, is upregulated, which increases the conversion of cholesterol to bile acids. This causes an increased demand for cholesterol in the liver cells, resulting in the dual effect of increasing transcription and activity of the cholesterol biosynthetic enzyme, hydroxymethyl-glutaryl-coenzyme A (HMG-CoA) reductase, and increasing the number of hepatic low-density lipoprotein (LDL) receptors. These compensatory effects result in increased clearance of LDL cholesterol (LDL-C) from the blood, resulting in decreased serum LDL-C levels (Grundy et al., *J Lab. Clin. Med.* 78:94–121 (1971); Shepherd et al., *New Engl. J Med.* 302:1219–1222 (1980)).

Clinical studies have demonstrated that elevated levels of total cholesterol (total-C), LDL-C, and apolipoprotein B (Apo B, a protein associated with LDL-C) are associated with an increased risk of atherosclerosis in humans. Similarly, decreased levels of high-density lipoprotein cholesterol (HDL-C) are associated with the development of atherosclerosis. Epidemiological investigations have established that cardiovascular morbidity and mortality vary directly with the levels of total-C and LDL-C, and inversely with the level of HDL-C.

The combination of colesevelam and an HMG-CoA reductase inhibitor is effective in further lowering serum total-C and LDL-C levels beyond that achieved by either agent alone.

Pharmacokinetics and Clinical Trials

Colesevelam is a hydrophilic, water-insoluble polymer that is not hydrolyzed by digestive enzymes and is not absorbed. In 16 healthy volunteers, an average of 0.05% of a single $^{14}$C-labeled colesevelam dose was excreted in the urine when given following 28 days of chronic dosing of 1.9 grams of colesevelam twice per day.

Colesevelam reduces total-C, LDL-C, and Apo B, and increases HDL-C when administered either alone or in combination with an HMG-CoA reductase inhibitor in patients with primary hypercholesterolemia.

Approximately 1,400 patients were studied in eight clinical trials with treatment durations ranging from 4 to 50 weeks. With the exception of one long-term study, all studies were multicenter, randomized, double-blind, and placebo-controlled. A maximum therapeutic response to colesevelam was achieved within 2 weeks and was maintained during long-term therapy.

In a study in patients with LDL-C between 130 and 220 mg/dL (mean 158 mg/dL), colesevelam was given for 24 weeks in divided doses with the morning and evening meals. As shown in Table 7 below, the mean LDL-C reductions were 15% and 18% at the 3.8 g and 4.5 g doses. The respective mean total-C reductions were 7% and 10%. The mean Apo B reductions were 12% in both treatment groups. Colesevelam at both doses increased HDL-C by 3%. There were small increases in triglycerides (TG) at both colesevelam doses that were not statistically different from placebo.

TABLE 7

Colesevelam 24 Week Trial- Percentage Change in Lipid Parameters From Baseline

| GRAMS/DAY | N | LDL-C | TOTAL-C | HDL-C | TG | APOB |
|---|---|---|---|---|---|---|
| Placebo | 88 | 0 | +1 | −1 | +5 | 0 |
| 3.8 g (6 tablets) | 95 | −15* | −7* | +3* | +10 | −12* |
| 4.5 g (7 tablets) | 94 | −18* | −10* | +3 | +9 | −12* |

*p < 0.05 for lipid parameters compared to placebo, for Apo B compared to baseline LDL-C, total-C, and Apo B are mean values; HDL-C and TG are median values.

In a study in 98 patients with LDL-C between 145 and 250 mg/dL (mean 169 mg/dL), colesevelam (3.8 g per day) was given for 6 weeks as a single dose with breakfast, a single dose with dinner, or as divided doses with breakfast and dinner. The mean LDL-C reductions were 18%, 15%, and 18% for the three dosing regimens, respectively. The reductions with these three regimens were not statistically different from one another.

Co-administration of colesevelam and an HMG-CoA reductase inhibitor (atorvastatin, lovastatin, or simvastatin) demonstrated an additive reduction of LDL-C in three clinical studies. As demonstrated in Table 8 below, colesevelam doses of 2.3 g to 3.8 g resulted in additional 8% to 16% reductions in LDL-C above that seen with the HMG-CoA reductase inhibitor alone.

TABLE 8

Colesevelam in Combination with Atorvastatin, Simvastatin, and Lovastatin; Percentage Change in Lipid Parameters

| DOSE/DAY | N | LDL-C | TOTAL-C | HDL-C | TG | APO B |
|---|---|---|---|---|---|---|
| Atorvastatin Trial (4-week): | | | | | | |
| Placebo | 19 | +3 | +4 | +4 | +10 | −2 |
| Atorvastatin 10 mg | 18 | −38* | −27* | +8 | −24* | −32* |
| colesevelam 3.8 g/ Atorvastatin 10 mg | 18 | −48* | −31* | +11 | −1 | −38* |
| Atorvastatin 80 mg | 20 | −53* | −39* | +6 | −33* | −46* |
| Simvastatin Trial (6-week): | | | | | | |
| Placebo | 33 | −4 | −2 | −3 | +6 | −4* |
| Simvastatin 10 mg | 35 | −26* | −19* | +3* | −17* | −20* |
| colesevelam/ Simvastatin 10 mg | 34 | −42* | −28* | +10* | −12* | −33* |
| Simvastatin 20 mg | 39 | −34* | −23* | +7* | −12* | −26* |
| colesevelam 2.3 g/ | 37 | −42* | −29* | +4* | −12* | −32* |

TABLE 8-continued

Colesevelam in Combination with Atorvastatin, Simvastatin, and Lovastatin; Percentage Change in Lipid Parameters

| DOSE/DAY | N | LDL-C | TOTAL-C | HDL-C | TG | APO B |
|---|---|---|---|---|---|---|
| Simvastatin 20 mg Lovastatin Trial (4-week): | | | | | | |
| Placebo | 26 | 0 | +1 | +1 | +1 | 0 |
| Lovastatin 10 mg | 26 | −22* | −14* | +5 | 0 | −16 |
| colesevelam 2.3 g/ Lovastatin 10 mg together | 27 | −34* | −21* | +4 | −1 | −24* |
| colesevelam 2.3 g/ Lovastatin 10 mg apart | 23 | −32* | −21* | +2 | −2 | −24* |

*$p < 0.05$ for lipid parameters compared to placebo, for Apo B compared to baseline LDL-C, total-C and Apo B are mean values; HDL-C and TG are median values.

In all three studies, the LDL-C reduction achieved with the combination of colesevelam and any given dose of HMG-CoA reductase inhibitor therapy was statistically superior to that achieved with colesevelam or that dose of the HMG-CoA reductase inhibitor alone.

The LDL-C reduction with atorvastatin (80 mg) was not statistically significantly different from the reduction achieved with the combination of colesevelam (3.8 g) and atorvastatin (10 mg).

Indications and Usage

Colesevelam, administered alone or in combination with an HMG-CoA reductase inhibitor, is indicated as adjunctive therapy to diet and exercise for the reduction of elevated LDL cholesterol in patients with primary hypercholesterolemia (Fredrickson Type IIa).

Therapy with lipid lowering agents should be a component of multiple risk-factor intervention in patients at significant increased risk for atherosclerotic vascular disease due to hypercholesterolemia. Lipid altering agents should be used in addition to a diet restricted in saturated fat and cholesterol and when the response to diet and other non-pharmacological means has been inadequate.

Prior to initiating therapy with colesevelam, secondary causes of hypercholesterolemia (i.e., poorly controlled diabetes mellitus, hypothyroidism, nephrotic syndrome, dysproteinemias, obstructive liver disease, other drug therapy, alcoholism) should be excluded, and a lipid profile obtained to assess total-C, HDL-C, and TG. For individuals with TG less than 400 mg/dL, LDL-C can be estimated using the following equation.

LDL-C=Total-C −[(TG/5)+HDL-C]

Serum cholesterol levels in patients should be periodically determined, as outlined in the National Cholesterol Education Program (NCEP) guidelines, to confirm a favorable initial and long-term response. The NCEP treatment guidelines are presented in Table 9.

TABLE 9

NCEP Guidelines

| | | LDL-C | |
|---|---|---|---|
| PATIENT ASSESSMENT CRITERIA | | Initiation level | Minimum Goal |
| Without CHD and with fewer than two risk factors | | ≧190 mg/dL | <160 mg/dL |
| Without CHD and with two or more risk factors | | ≧160 mg/dL | <130 mg/dL |
| With CHD | | ≧130 mg/dL | ≦100 mg/dL |

CHD = Coronary Heart Disease
1. Other risk factors for CHD include the following: age (males >45 years, females >55 years or premature menopause without estrogen replacement therapy); family history of premature CHD; current cigarette smoking; hypertension; confirmed HDL-C, <35 mg/dL <<0.01 mmol/L); and diabetes mellitus. Subtract risk factor if HDL-C >60 mg/dL (>1.6 mmol/L).
2. In CHD patients with LDL-C levels of 100–129 mg/dL, the physician should exercise clinical judgment in deciding whether to initiate drug treatment.

Dosage and Administration

Monotherapy

The recommended starting dose of colesevelam is 3 tablets taken twice per day with meals or 6 tablets once per day with a meal. The colesevelam dose can be increased to 7 tablets, depending upon the desired therapeutic effect. Colesevelam should be taken with a liquid.

Combination Therapy

Colesevelam, at doses of between about 4 and about 6 tablets per day, has been shown to be safe and effective when dosed at the same time (i.e., co-administered) as an HMG-CoA reductase inhibitor, or when the two drugs are dosed apart. For maximal therapeutic effect in combination with an HMG-CoA reductase inhibitor, the recommended dose of Colesevelam is 3 tablets taken twice per day with meals or 6 tablets taken once per day with a meal.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating Syndrome X in a patient in need thereof, comprising administering to said patient a therapeutically effective amount of colesevelam or a pharmaceutically acceptable salt thereof, alone or in combination with an antihyperlipidemic agent; a plasma HDL-raising agent; an antihypercholesterolemic agent; an acyl-coenzyme A: cholesterol acyltransferase (ACAT) inhibitor; a cholesterol absorption inhibitor; a bile acid sequestrant anion exchange resin; an LDL (low density lipoprotein) receptor inducer; a fibrate; vitamin $B_6$ (also known as pyridoxine) or a pharmaceutically acceptable salt thereof; vitamin $B_{12}$; an antioxidant vitamin; an angiotensin II antagonist converting enzyme inhibitor; or a platelet aggregation inhibitor.

2. A method for treating Syndrome X in a patient in need thereof, comprising administering to said patient a therapeutically effective amount of sevelamer or a pharmaceutically acceptable salt thereof.

* * * * *